US006358246B1

(12) United States Patent
Behl et al.

(10) Patent No.: US 6,358,246 B1
(45) Date of Patent: *Mar. 19, 2002

(54) METHOD AND SYSTEM FOR HEATING SOLID TISSUE

(75) Inventors: Robert S. Behl, Palo Alto; Eben L. Kermit, Menlo Park; Peter F. Lyons, San Jose; Colin J. Nichols, Fremont, all of CA (US)

(73) Assignee: Radiotherapeutics Corporation, Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/344,822

(22) Filed: Jun. 25, 1999

(51) Int. Cl.⁷ ................................................ A61B 18/04
(52) U.S. Cl. ............................ 606/34; 606/49; 606/27; 606/32; 607/96

(58) Field of Search ....................... 606/32, 34, 37–42, 606/45, 49, 27–29; 607/96, 98, 99, 113; 604/49, 114

*Primary Examiner*—Roy Gibson
(74) *Attorney, Agent, or Firm*—Townsend and Townsend and Crew LLP

(57) ABSTRACT

Methods for heating tissue by delivering radio frequency energy through tissue electrodes comprise controlling energy delivery so that an abrupt increase in impedance between the electrodes and the tissue is observed, typically in the form of an abrupt decrease in power delivered to the electrodes. The power at which the impedance increases and/or the time required to induce such an increase in impedance, are relied on to determine acceptable ranges to achieve a maximum sustainable delivery of radio frequency energy to the tissue consistent with complete, rapid, and uniform heating of the tissue.

50 Claims, 8 Drawing Sheets

METHOD AND SYSTEM FOR HEATING SOLID TISSUE

BACKGROUND OF THE INVENTION

1. Field of the Invention

The present invention relates generally to the use of radio frequency energy for heating and necrosing solid tissue. More particularly, the present invention relates to a control method and system for delivering radio frequency current to the tissue through an electrode or electrode array disposed within the tissue.

The delivery of radio frequency energy to target regions within solid tissue is known for a variety of purposes. Of particular interest to the present invention, radio frequency energy may be delivered to diseased regions in target tissue for the purpose of tissue heating and/or necrosis, referred to generally as hyperthermia. For example, the liver is a common depository for metastases of many primary cancers, such as cancers of the stomach, bowel, pancreas, kidney and lung. Electrosurgical probes for deploying single and multiple electrodes have been designed for the treatment and necrosis of tumors in the liver and other solid tissues. See, for example, the references cited in the Description of the Background Art hereinafter.

A primary goal in such hyperthermic treatments, particularly those intended for tumor treatment, is the complete, thorough, and uniform heating of the target tissue mass. Uniform heating of the tissue mass, however, can be difficult to achieve, particularly in highly vascularized tissues where variability in local blood flow can have a significant effect on the heating characteristics of the tissue. For example, creation of a lesion having a selected volume in some highly perfused tissue locations may require twice as much power as an identically-sized lesion in less highly perfused locations. While a variety of approaches for achieving such complete, thorough, and uniform heating of tissue have been proposed, most such approaches are somewhat complex and require the use of electrodes which are capable of measuring temperature, impedance, or the like. See, for example, the radio frequency power supply described in published PCT Application WO 93/08757. In general, many approaches for achieving uniform tissue heating have relied on slow, gradual heating of the tissue in order to avoid the formation of charred or otherwise necrosed, high radio frequency impedance regions within the target tissue mass. Such approaches, however, are complex, can result in an undesirable prolongation of the treatment, and are not always successful.

For these reasons, it would be desirable to provide improved treatment methods, systems, and apparatus which allow for effective and efficient delivery of a radio frequency energy to solid tissue masses using electrodes. In particular, it would be desirable to provide such methods, systems, and apparatus which are useful with many or all tissue-penetrating electrode systems which are now available or which might become available in the future. The methods, systems, and apparatus should be simple to implement and use, and should preferably reduce the complexity, cost, and treatment time required to achieve complete heating and/or necrosis of the target tissue mass. The methods, systems, and apparatus should preferably require no information or feedback from the tissue region being treated, other than information which can be acquired from the power delivery characteristics which can be monitored in the radio frequency power delivery system itself. In particular, the methods, systems, and apparatus should be able to operate solely by monitoring the power and/or current delivery characteristics of the radio frequency energy into an electrode system present in the target tissue. At least some of these objective will be met by the present invention as claimed hereinafter.

2. Description of the Background Art

The heating of solid tissue with radio frequency current using the preferred electrode structures of the present invention is described in WO 96/29946 and co-pending applications Ser. Nos. 08/410,344; 08/559,072; 08/766,154; 08/764,085; and 08/858,414, filed on May 19, 1997, the full disclosures of which are incorporated herein by reference.

WO 97/06739; WO 97/06740; WO 97/06855; and WO 97/06857 describe RF treatment electrodes and note that power delivery can "impede out" if levels are raised too high.

Assignee of the present application has developed a radio frequency power supply (Model RF-2000, RadioTherapeutics Corporation, Mountain View, Calif.) which provides power levels up to 100 W and is intended for the coagulation (ablation) of soft tissue. The power supply is controlled by a programmable microprocessor which is capable of continuously monitoring power delivered to an electrode system.

Patents and published applications describing radio frequency tissue ablation using electrodes having various configurations include U.S. Pat. Nos. 5,662,680; 5,599,346; 5,599,345; 5,562,703; 5,536,267; 5,489,161; 5,472,441; and 5,458,597; and published International Applications WO 97/06857; WO 97/06855; WO 97/06740; WO 97/06739; WO 96/04860; and WO 95/13113.

A radio frequency power supply having impedance monitoring capability is described in WO 93/08757.

Other radio frequency power apparatus and methods are described in U.S. Pat. Nos. 5,556,396; 5,514,129; 5,496,312; 5,437,664; and 5,370,645; and WO 95/20360, WO 95/09577, and WO 95/20360.

SUMMARY OF THE INVENTION

The present invention provides improved methods, systems, and apparatus for delivering radio frequency energy to electrodes disposed in tissue for inducing hyperthermia and other purposes. It has been found that the delivery of radio frequency power to electrode(s) disposed in tissue can, if the power is delivered for a sufficient time and/or at a sufficient power delivery level or flux, result in an abrupt increase in the electrical impedance between the electrode(s) and tissue. While such an abrupt increase in impedance is undesirable since it results in an immediate fall-off of energy delivery (for a voltage limited radio frequency power source), the present invention relies on the occurrence of the abrupt reduction in power delivery (which may be observed as a reduction in current delivery to the electrodes) to provide information about the heat capacity and heat delivery characteristics of the local target tissue region. The present invention uses such information to control subsequent delivery of energy to the target tissue region using the same electrode(s).

The present invention still further depends, in least in part, on the observation that the abrupt rise in the electrode-tissue interface impedance diminishes very rapidly when the power delivery is stopped, typically disappearing within several seconds. Delivery of the radio frequency power can be resumed after the impedance has diminished, typically to impedance levels substantially equal to those observed prior to the abrupt increase. Based on these observations, it is possible to determine improved or optimized radio frequency power delivery levels and protocols based on the power levels and/or time periods required to induce the abrupt impedance increases and associated power declines in specific target locations. In particular, the protocols rely on appropriate adjustments to the power levels which are resumed after the tissue impedance diminishes.

It is presently believed that the abrupt increase in electrode-tissue interface impedance results from the formation of a thin gaseous layer over the electrode surface, apparently resulting from vaporization of water within the tissue as the temperature approaches the local boiling point. Surprisingly, the thin gaseous layer appears to spread from an initial nucleation site to cover most or all of an electrode surface in a very short time period, typically less than 30 seconds, resulting in an increase in electrode-tissue interface impedance which is very large when compared to the total system impedance prior to formation of the thin gaseous layer. In the exemplary systems described herein after, typical system impedance prior to formation of the thin gaseous layer will be in the range from 40Ω to 70Ω, which impedance will rise to from 300Ω to 400Ω after formation of the thin gaseous layer. While this is presently believed to be the mechanism responsible for the above-described observations, the present invention does not depend on the accuracy of this model. The methods, systems, and apparatus of the present invention have been found to be useful and effective regardless of the actual mechanism which is responsible for the change in impedance.

In a first particular aspect of the present invention, a method for heating tissue and/or controlling the delivery of radio frequency energy to an electrode and tissue comprises gradually increasing the power delivery rate to the tissue over time until an abrupt decrease in the power delivery rate (resulting from the increase in electrode-tissue interface impedance) is observed. The power which such power drop occurs can be determined, and is considered a "maximum" power level which should not be exceeded. After waiting for the electrode-tissue impedance to return to an acceptable level, typically requiring fifteen seconds or less, the electrodes can be reenergized and the power delivery to tissue resumed at a level which is some fraction of the maximum power delivery rate. Typically, the reenergization power level is from 50% to 90% of the maximum power level, preferably being from 70% to 80%. The increase in the power delivery rate used to determine the maximum power level will depend on the electrode size as well as the initial power level, typically being linear and increasing at a rate in the range from 1 W/min. to 25 W/min., preferably from 5 W/min. to 10 W/min.

In a second aspect of the present invention, a method for determining the subsequent level of power delivery relies on rapidly increasing the level of power delivered to the tissue to an amount which has been predetermined to certainly or very likely produce the abrupt impedance increase/power delivery decrease almost immediately after the power increase is initiated, typically within 10 seconds, preferably within 5 seconds. While the time between initiating the power increase and observing the power decrease will be relatively short, it will be finite and measurable. The elapsed time between such initiation and the observed power decrease is relied on by the present invention as an indicator of the margin between an equilibrium or gradually increasing electrode/tissue interface temperature and a maximum electrode/tissue interface temperature characteristic of that particular target tissue location.

By establishing an initial level of radio frequency power delivered to the target tissue mass, a relatively stable (equilibrium) or gradually increasing electrode/tissue interface temperature is achieved. By then rapidly increasing or pulsing the energy delivery rate to induce the impedance increase/power decrease, the time required to induce the event provides a qualitative determination of how close the initial treatment temperature was to a "maximum" characteristic of that tissue location. This qualitative determination, in turn, can be relied on for raising, lowering, or maintaining the initial level of power delivery to the tissue. In particular, if the power decrease/impedance increase occurs almost immediately after the delivered power is rapidly increased, e.g. within 2 seconds to 5 seconds, usually from 2 seconds to 3 seconds, it can be assumed that the treatment conditions prior to the power increase had resulted in a tissue temperature which is very close to the maximum. Thus, in order to achieve uniform and complete heating of the tissue, it will be desirable to decrease the power delivery rate to the tissue from the initial rate to delay formation of the thin gaseous layer. Conversely, if the power decrease/impedance increase requires a relatively long time period to occur, for example from 10 seconds to 20 seconds, it can be assumed that the initial tissue temperature is relatively far from the maximum sustainable by the tissue. Thus, it will be desirable to increase the power delivery rate in order to achieve optimum tissue hyperthermia. There may also be instances, of course, where the elapsed time between power increase to power decrease/tissue impedance increase will be considered within an acceptable or optimum range, where the initial treatment power level need not be modified. In this second aspect of the present invention, it can be seen that the power level used for the subsequent treatment of the tissue mass will vary inversely with respect to the observed length of the elapsed time.

In general, the radio frequency energy will be supplied as a radio frequency current using a controlled voltage or constant voltage power supply. The use of such radio frequency power sources is preferred because the limited voltage available necessarily results in a reduction of current when the electrode/tissue impedance rises. In addition to allowing the monitoring of impedance based on observing the power or current delivered to the electrodes, the limited voltage also decreases the likelihood of arcing or sparking from the electrode into the tissue. Usually, the power supply will be operated at a level which depends on the size of the electrode, the target tissue type, and the degree of tissue perfusion. Typically, the power supply will provide power in the range from 10 W to 200 W, during all phases of the above-described methods. For prolonged treatment, the electrodes will generally be energized at a power between 20 and 100 W which is in the range from 50% to 90% of the local maximum power level, usually from 70% to 80%.

In further aspects of the present invention, systems are provided which comprise an electrosurgical power supply, typically a radio frequency power supply, in combination with written, electronic, or other instructions setting forth any of the methods set forth above.

In still another aspect of the present invention, computer programs embodied in a tangible medium, such as a floppy disk, compact disk, tape, flash memory, hard disk memory, or the like, which set forth any of the methods described above, in computer-readable code. Such computer programs are useful with digital controllers which may be built into a radio frequency power supply or other electrosurgical power supply according to the present invention. Alternatively, such programs may be useful with general purpose computers, such as personal computers, which can be interfaced with conventional electrosurgical power supplies for the control thereof according to any of the methods of the present invention.

In a still further aspect of the present invention, electrosurgical power supplies are provided which comprise a radio frequency power source having a voltage controlled output, a connection for a tissue electrode, and a connection for a return or counter electrode. The electrosurgical power supplies will further comprise a digital controller or other means for automatically adjusting the power output of the power supply, where the power is delivered between an electrode and a counter electrode, where the electrodes are coupled to the power supply and present in solid tissue. The controller or other adjusting means is programmed or programmable to automatically increase power delivered by the radio frequency power source into a target tissue mass to a maximum level where an abrupt rise in impedance occurs. After the abrupt rise is observed, the controller or other adjusting means will reduce the power delivered by the radio frequency power source to a level below that at which the increase in impedance is maintained. After allowing the impedance to decrease, a controller or other adjusting means will increase or reestablish a treatment power level which is below the maximum level observed, but which may be higher or lower than any initial treatment level employed before the power is pulsed. In particular, the controller or other adjusting means can be programmed to implement any of the methods described above independent of operator intervention.

DESCRIPTION OF THE SPECIFIC EMBODIMENTS

Figure 1:
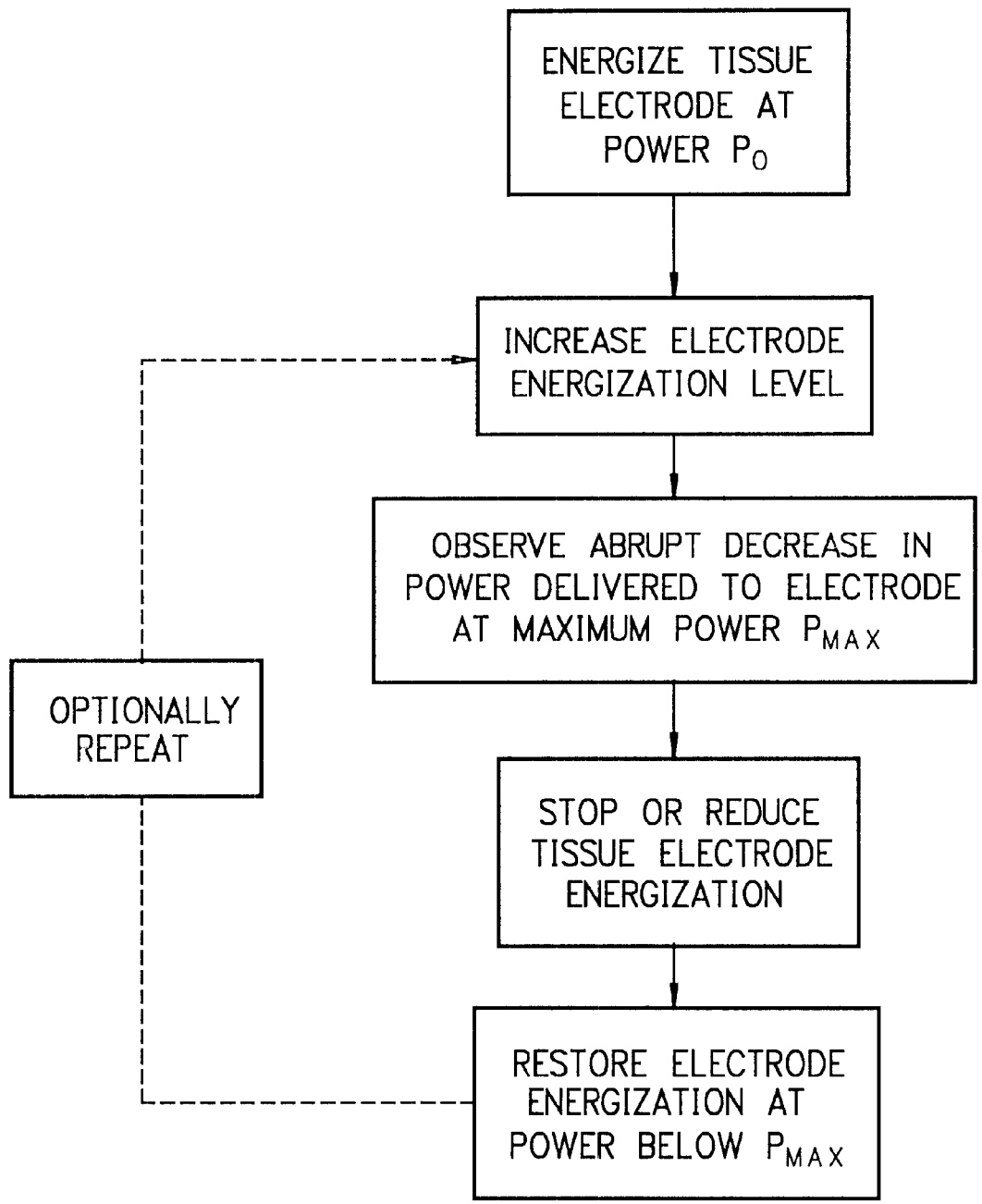
FIG. 1 is a flow chart illustrating the method steps of the present invention which may be implemented manually or as part of an automatic control system, as described in more detail below.

Methods, systems, and apparatus according to the present invention will rely on placement and use of one or more electrode element(s) positioned at or within a treatment region within solid tissue of a patient. The treatment region may be located anywhere in the body where hyperthermic exposure may be beneficial. Most commonly, the treatment region will comprise a solid tumor within an organ of the body, such as the liver, kidney, lung, bowel, stomach, pancreas, breast, prostate, uterus, muscle, and the like. The volume to be treated will depend on the size of the tumor or other lesion, typically having a total volume from 1 $cm^3$ to 150 $cm^3$, usually from 1 $cm^3$ to 50 $cm^3$, and often from 2 $cm^2$ to 35 $cm^2$. The peripheral dimensions of the treatment region may be regular, e.g. spherical or ellipsoidal, but will more usually be irregular. The treatment region may be identified using conventional imaging techniques capable of elucidating a target tissue, e.g. tumor tissue, such as ultrasonic scanning, magnetic resonance imaging (MRI), computer-assisted tomography (CAT), fluoroscopy, nuclear scanning (using radio labeled tumor-specific probes), and the like. Preferred is the use of high resolution ultrasound which can be employed to monitor the size and location of the tumor or other lesion being treated, either intraoperatively or externally.

Treatments according to the present invention will usually be effected by passing a radio frequency current through the target tissue region in a monopolar or bipolar manner. The specific electrode probes and methods described hereinafter illustrate a monopolar application of radio frequency current to the patient, where a treatment electrode is positioned in the target tissue and a passive or dispersive "electrode" is disposed against the patient's skin to complete a return path for the radio frequency circuit being created. Alternatively, a type of monopolar operation may be employed where the dispersive return electrode is mounted on a portion of the electrode probe being used for treatment. In that case, the area of the dispersive electrode is maximized in order to decrease any heating effect which might occur from current flux at the return electrode. Further alternatively, the methods of the present invention can employ bipolar treatment where paired treatment electrodes are employed to both form the complete circuit and to heat the tissue therebetween.

The desired radio frequency power may be supplied by a conventional or modified general purpose electrosurgical power supply operating at a frequency in the range from 300 kHz to 1.2 MHz, with a conventional sinusoidal or non-sinusoidal wave form. Preferably, the power supply will operate with a fixed or controlled voltage so that power and current diminish with an increase in observed impedance. Preferred power supplies will operate at relatively low fixed voltages, typically below 150 V (peak-to-peak), usually being from 50 V to 100 V will be preferred. Such radio frequency power supplies are available from Radionics. In all cases, current will be selected to provide an operating power generally in the range from 10 W to 100 W, usually have a sine wave form, but optionally having other wave forms.

The radio frequency power supplies will have adjustable power outputs, typically by varying the voltage to set current and power, and will permit monitoring of the actual power delivered to the electrodes being used to treat the patient. It will be appreciated that with a fixed or controlled voltage, the power delivered will depend on the current and the impedance present in the circuit. Generally, as described in detail below, methods according to the present invention will begin with delivering power at levels which do not result in excessive electrode/ tissue interface impedances. At some point in the treatment protocols of the present invention, power/current will be increased resulting in a more rapid heating of the tissue. Such rapid heating will induce an abrupt increase in the impedance between the tissue electrodes and the adjacent tissue, as previously described. The power supply operates at a constant voltage and will thus be unable to maintain current/power levels through the increased tissue impedance. Thus, power is reduced rapidly since it falls as the square of the decrease in current.

Preferably, the power supplies will be programmable or be capable of being interfaced with a digital controller, such as a personal computer. An exemplary power supply having the power and computer interface capabilities suitable for the present invention is the Model RF-2000, available from RadioTherapeutics Corporation, Mountain View, Calif., assignee of the present application.

Referring now to FIG. 1, methods according to the present invention will be generally described. Such methods will rely on energizing tissue electrodes disposed within tissue to heat the tissue for a variety of hyperthermic therapeutic purposes. The electrode(s) will be energized with radio frequency current generally within the power ranges set forth above. Initially, the electrode(s) will be energized at a power $P_0$, with an initial energization lasting long enough to establish a base tissue temperature, which may either be constant or may be gradually increasing, i.e. at a rate less than about 10° C./min., usually less than about 5° C. The electrode energization will then be increased above the initial power level $P_0$, by either a rapid increase or gradual increase protocol as described in more detail below. In both protocols, the level of power delivered to the tissue will eventually cause an abrupt increase in the impedance between the electrode(s) and the adjacent tissue, which in turn results in observation of an abrupt decrease in the power delivered to the electrode(s). Conveniently, the decrease in power is observable by measuring the current and voltage, thus permitting determination of power delivered from the power supply. Thus, there is no need to measure impedance, temperature, or any other characteristics directly within the tissue or at the electrode/tissue interface. Power at which such decrease occurs is defined herein as the maximum power $P_{MAX}$. The abrupt increase in impedance and decrease in power delivered to the electrode(s) is dependent on a number of factors such as tissue type, the degree of local blood perfusion, and the tissue temperature prior to the power increase. In all cases, at the local value of $P_{MAX}$, the abrupt impedance/power decrease will occur over a very short period of time, typically in the range from 10 seconds to 20 seconds. The increase in impedance results from the formation of a thin layer of gas over the electrodes which begins as discrete, isolated bubble(s) at particular sites on the electrode surface. Surprisingly, such local bubble formation quickly spreads over most or all of the electrode surface area so that the power delivered to the electrodes quickly drops to a uniformly low density. Thus, power delivered to the tissue will be reduced, typically by an amount in the range from 70% to 95%, usually in the range from 85% to 95%, based on the initial power level $P_0$.

Determination of the maximum power level is useful in a variety of ways to determine a subsequent treatment power level, as described in more detail below. In all treatment protocols, however, it will be necessary to briefly stop or reduce the delivery of energy to the tissue through the electrode(s). As discussed above, it is believed that the impedance results from a very thin gaseous layer formed over all or a portion of the electrode surface, and it is further believed that cessation of energization allows the thin gaseous layer to cool very rapidly and to dissipate. Usually, the radio frequency power source will be completely de-energized for a period of time sufficient to permit the bubble layer to dissipate and the tissue impedance to return to its low impedance condition, typically from 3 seconds to 20 seconds, usually from 5 seconds to 10 seconds. It is not necessary, however, to completely shut off power so long as it is reduced sufficiently to allow the temperature and impedance to lower.

After the impedance has returned to its low impedance state, the energization of the electrode(s) will be restored at a power level selected to maximize delivery of radio frequency energy to the target tissue without prematurely terminating treatment due to the high impedance/low power delivery condition described above. In some cases, however, it will be desirable to optionally repeat the intentional inducement of the high impedance/low power delivery state in order to further optimize power delivery, as discussed in more detail below.

Figure 2:
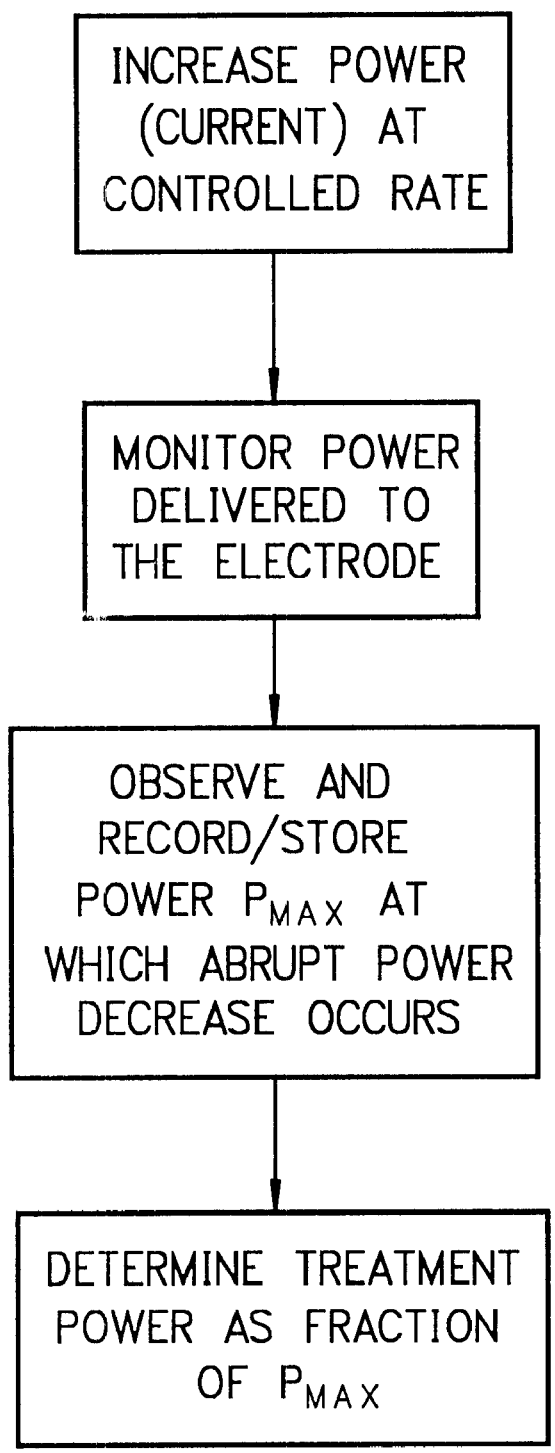
FIG. 2 is a flow chart illustrating a first exemplary method for determining a treatment power level which may be implemented as part of the general method illustrated in FIG. 1.

Referring now to FIG. 2, a first preferred protocol for inducing the abrupt impedance increase/power decrease and determining a desired treatment power level is described. Power being delivered to the tissue electrodes is increased at a controlled rate, typically in the range from 1 W/min. to 25 W/min., preferably from 10 W/min. to 15 W/min. The power is preferably increased linearly at a specific rate within these ranges via a linear increase in voltage until the impedance increases. Actual power delivered to the electrode is monitored, either visually by the operator or automatically by a control system. At some point, which may occur from 2 minutes to 10 minutes after initiating the power increase, usually occurring from 3 minutes to 5 minutes after the initiation of the power increase, the impedance at the electrode-tissue interface will abruptly increase, causing an observable decrease in the level of power being delivered to the electrodes. The power which was delivered to the electrodes immediately prior to the abrupt decrease is considered to be the maximum power ($P_{MAX}$) deliverable to the electrodes for that particular treatment location. The subsequent treatment power level can thus be determined as a fraction or percentage of the maximum power $P_{MAX}$, typically being from 50% to 90% of $P_{MAX}$, preferably from 70% to 75% of $P_{MAX}$.

The particular protocol illustrated in FIG. 2 is desirable in its simplicity. It can readily be implemented manually, i.e. without the use of an automatic digital controller, by a user gradually increasing the delivered power rate by manually adjusting the power supply (either continuously or more usually in shortly spaced increments within the ranges set forth above), but is also suitable for automatic implementation. It is disadvantageous, however, in that it takes a relatively long time to identify $P_{MAX}$, taking a particularly long time in highly vascularized tissue in which the electrode/tissue interface temperature rises slowly at lower power levels. With automation, the power may be increased in a non-linear manner, e.g. exponentially. The exponential power increase will shorten the time necessary to observe the decrease in power delivery, but will be more difficult to assess in terms of the desired, target power delivery to tissue. That is, by increasing the rate of increase in power delivery, the margin of difference between the beginning tissue temperature and the end tissue temperature is more difficult to determine and utilize.

Figure 3:
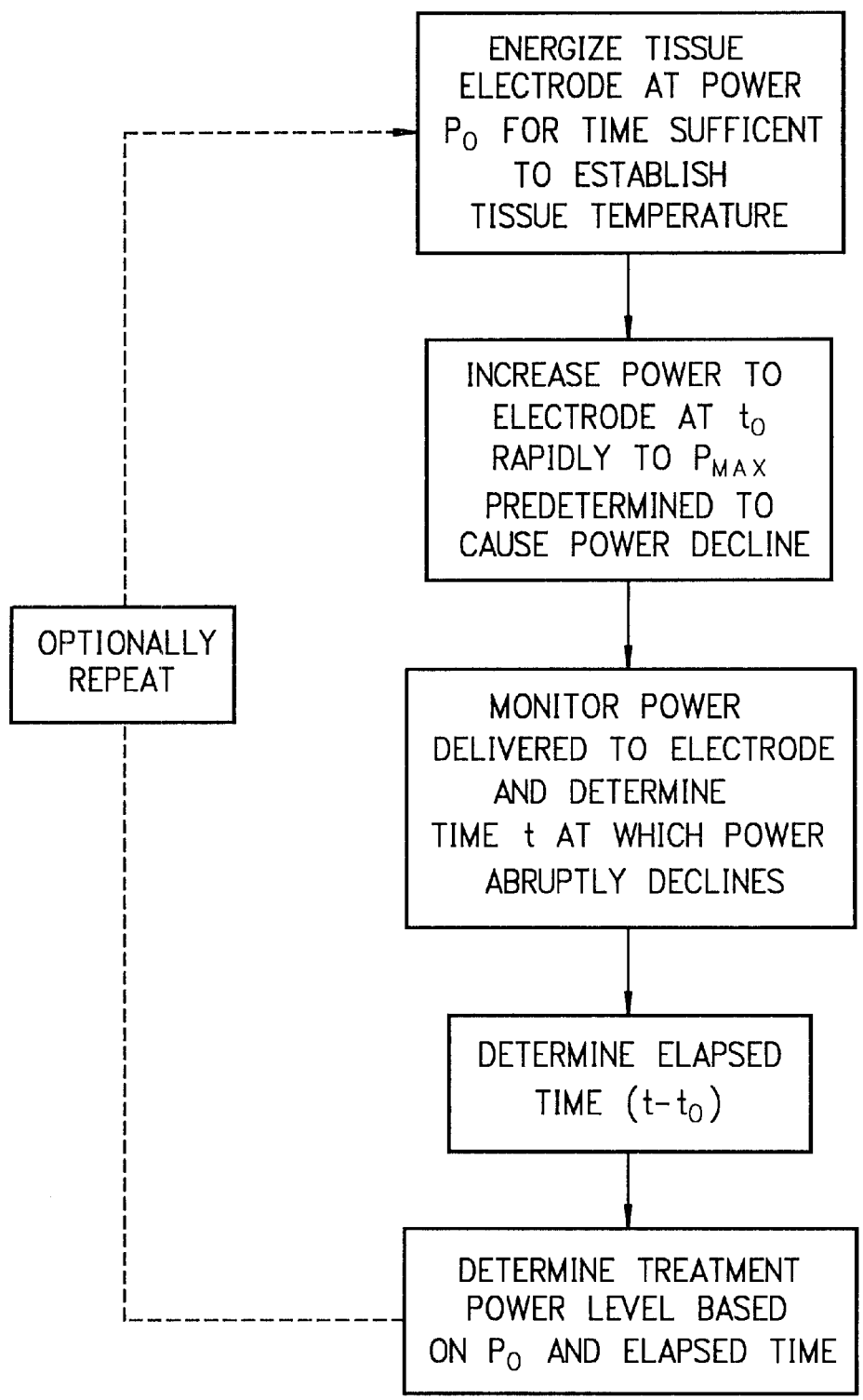
FIG. 3 is a flow chart illustrating a second exemplary method for determining a treatment power level which may be implemented as part of the general method set forth in FIG. 1.

An alternative protocol for determining both maximum power and a desired treatment power level is illustrated in FIG. 3. The protocol of FIG. 3 energizes the tissue electrode at a power Po selected to be below the maximum power level $P_{MAX}$ in all circumstances, i.e. for all possible perfusion levels in the target tissue. In the case of a 3.5 cm electrode array described hereinafter, the $P_0$ will typically be selected to be 50 W or less. $P_0$ is applied for some minimum period of time, typically at least about 3 minutes, usually at least about 5 minutes. Thus, an electrode/tissue interface temperature is established, which may be a substantially steady state temperature or may be a gradually increasing temperature. Thereafter, the electrode energization level is rapidly increased to a predetermined power above that expected to be sufficient to induce the impedance increase/power decrease. Typically, the power is increased over a very short period of time, from 0.5 seconds to one second, most preferably being increased as a spike, and the increased power level is typically above 80 W, usually being above 100 W, and most usually being in the range from 100 W to 120 W for a typical 3.5 cm diameter spherical treatment volume. Specific power levels, of course, will depend on the particular tissue being treated and size of electrode being used. After the power is increased to the target level, the time elapsed until the power delivered to the electrodes decreases is determined. The length of the elapsed time is a direct indication of the difference between the initial tissue temperature and a maximum temperature at which local tissue impedance increases. Thus, observation of a relatively long time period between the power increase to the electrode and observed decrease of delivered power (e.g. 20 seconds to 30 seconds, indicates that an increased treatment power level can be used. Conversely, a short time between the power increase and observed decrease in delivered power (e.g. 3 seconds to 5 seconds) indicates that the initial tissue temperature is relatively close to its maximum value and that a decreased power level should be employed to ensure heating of the tissue in a complete and uniform manner. Times between these ranges, i.e. greater than 5 seconds but less that 20 seconds, generally indicate that the treatment power level prior to the rapid increase was generally in the right range. Of course, times to decrease which are closer to 5 seconds than 20 seconds may warrant some decrease in the subsequent treatment power level, while those which are closer to 20 seconds than 5 seconds may warrant some increase in the treatment power level.

The protocol of FIG. 3 will often be repeated one or more times in order to adjust the treatment power level during subsequent portions of the treatment. It will be appreciated that each time the protocol is repeated, the qualitative difference between the tissue temperature which has been achieved (which will increase as the treatment progresses) and the maximum tissue temperature will be determined. Each of these readings will permit further adjustment of the treatment power level in order to maximize the total amount of energy and the uniformity of heat being delivered to the tissue.

Figure 4:
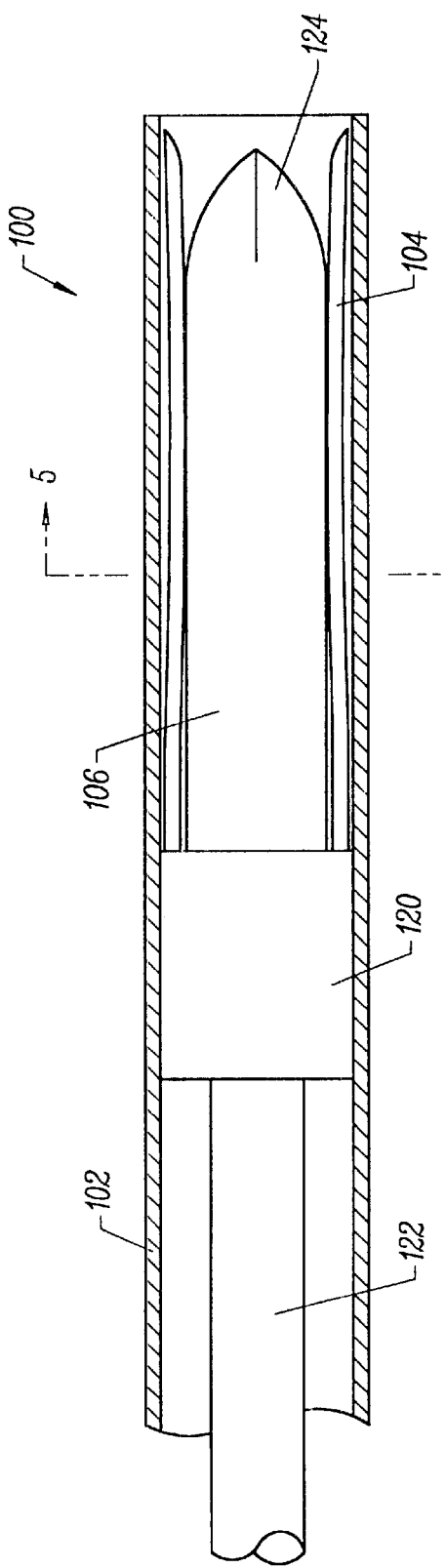
FIG. 4 is illustrates the distal end of an electrode probe assembly which may be employed in the methods and systems of the present invention.
Figure 6:
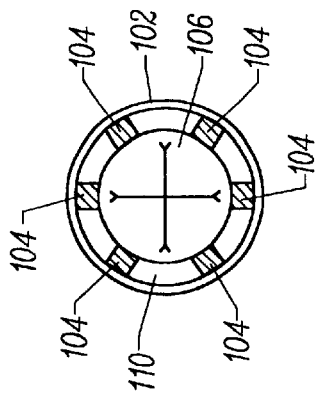
FIG. 6 is an end view of the distal tip of the probe of FIG. 4.
Figure 5:
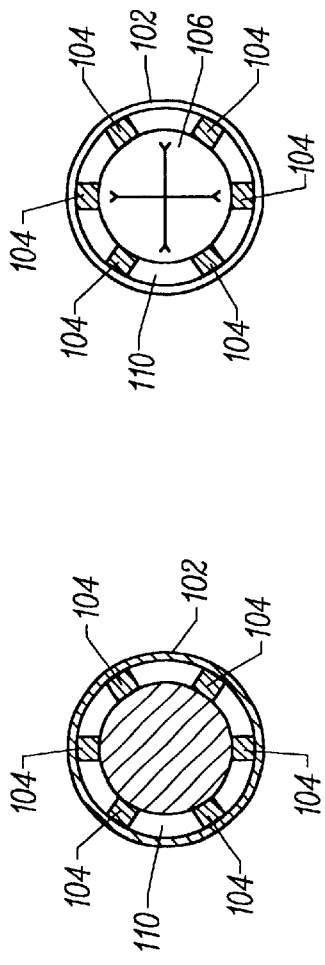
FIG. 5 is a cross-sectional view taken along line 5—5 of FIG. 4.

Referring now to FIGS. 4–6, a particular electrode assembly for use in the methods of the present invention will be described. A probe system 100 includes a cannula 102 and a plurality of individual electrodes 104 constrained within the cannula over the outer cylindrical surface of a core member 106. The cannula 102 is only partly illustrated with a proximal length broken-off. The entire cannula will typically have a length in the range from about 5 cm to 30 cm, preferably from 10 cm to 20 cm, and outer diameter in the range from 1 mm to 5 mm, preferably from 1.3 mm to 4 mm, and an inner diameter in the range from 0.7 mm to 4 mm, preferably from 1 mm to 3.5 mm. The cannula may be formed from metals, plastics, or the like, and may be electrically active or inactive within the probe system, depending on the manner in which electrical energy is to be applied.

The individual electrodes 104 are illustrated as having rectangular cross-sectional geometries, with preferred dimensions generally within the ranges set forth above. The electrodes 104 are resilient and have a spring memory which causes them to curve along an arcuate path as they are distally extended from the cannula 102, as shown in FIGS. 13–16 hereinafter.

An annular envelope 110 is defined between the inner surface of the cannula 102 and the outer surface of core member 110, as best seen in FIGS. 5 and 6. The width of the annular envelope 110 (defined by the distance between the outer surface of core 106 and inner surface of cannula 102) as typically in the range from 0.1 mm to 1 mm, preferably from 0.15 mm to 0.5 mm, and will usually be selected to be slightly larger than the thickness of the individual electrodes 104 in the radial direction. In this way, the electrodes are constrained and held in generally axially aligned positions within the cannula 102.

Electrodes 104 are connected at their proximal ends to a cylindrical block 120 which in turn is secured to the distal end of a reciprocatable shaft 122. The core 106 is also secured to the distal end of cylindrical block 120 so that the core and electrodes move together as the shaft 122 is advanced distally or retracted proximally relative to the cannula 102. As the core 106 moves with the electrodes, it will be appreciated that the core will enter the tissue at the same time as the electrodes 104. Thus, the core 106 is shown to have a sharpened distal end 124 to enhance tissue penetration. The core 106 may be electrically coupled to the electrodes 104 (in which case it acts as an additional electrode of the same polarity as electrodes 104) or may be electrically isolated from the electrodes. When the core is electrically isolated, it can remain neutral during a treatment protocol, or alternatively it may be energized in the opposite polarity and thus act as a return electrode in a bipolar treatment protocol.

Note that a total of six electrodes are illustrated. Additional electrodes could be added in the spaces between the illustrated electrodes, with the maximum number of electrodes determined by the electrode width and total circumferential distance available (i.e., the electrodes could be tightly packed). It would also be possible to add additional concentric layers of electrodes, although such a design will generally not be preferred.

Figure 10:
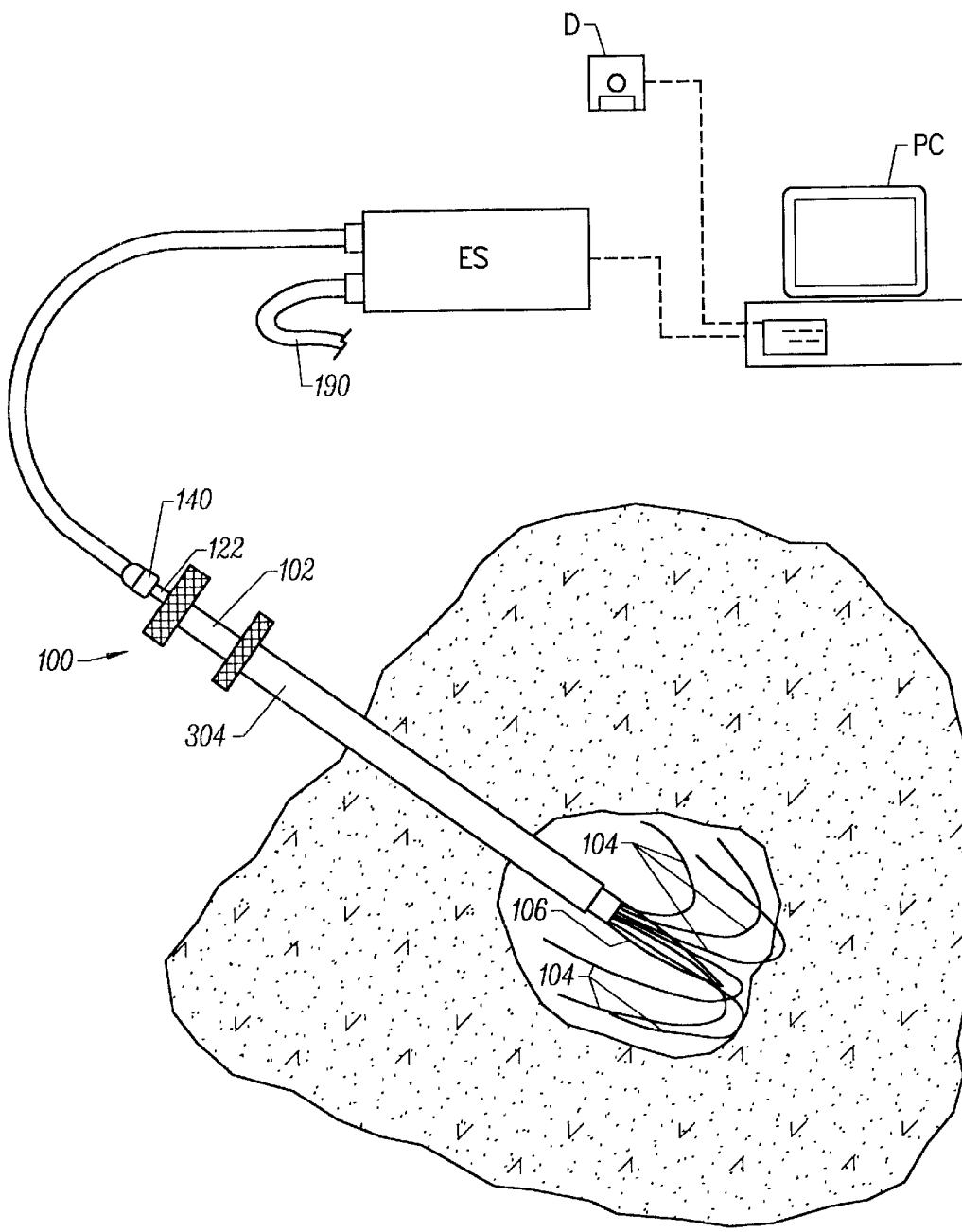

As discussed above, the electrosurgical power supply ES may be a conventional or modified power supply, depending on the desired implementation of the methods of the present invention. The methods may be performed manually, i.e. by an operator manually adjusting the power levels and observing the power deliveries on a conventional power supply. Alternatively and preferably, the methods of the present invention may be implemented using a digital controller which may be incorporated within the electrosurgical power supply ES, situated between the electrosurgical power supply and the patient, or which may be interfaced with a properly equipped power supply. The use of a computer interfaced with a power supply is illustrated in FIG. 10. The power supply ES will also usually include a monitoring/control interface. The computer PC may employ any operating system compatible with the electrosurgical power supply ES, the computer will typically be interfaced using a conventional cable. The methods of the present invention may be delivered to the personal computer PC and thus to the electrosurgical power supply ES by programming the computer in any conventional manner. A floppy disk D or other computer memory component may be used in order to implement the program within the computer. Any other manner of delivering computer readable code and instructions into the computer may also be utilized, including compact disk, tape, read only memory (ROM), and delivery of instructions via a modem and/or over the internet.

Figure 7:
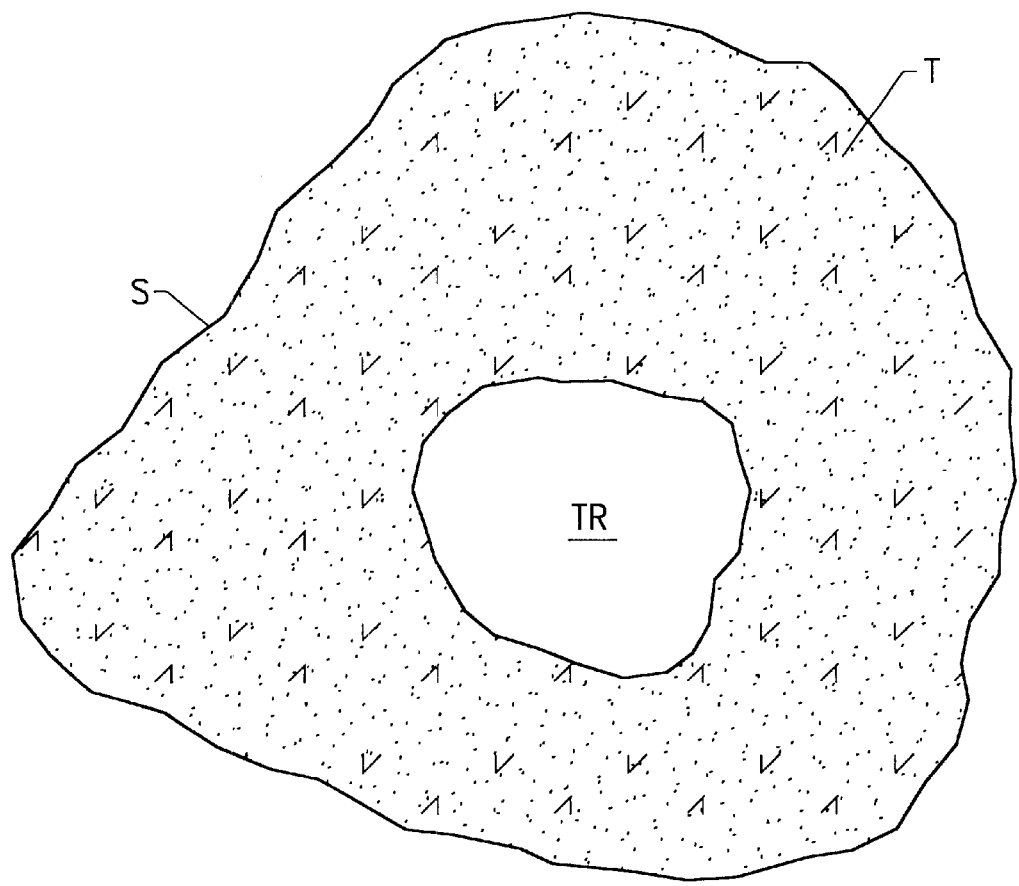
FIGS. 7–10 illustrate use of the probe of FIG. 4 in treating a tissue target region according to the methods of the present invention.

Referring now to FIGS. 7–10, a treatment region TR within tissue T is located beneath the skin or an organ surface S of a patient. The treatment region TR may be a solid tumor or other lesion where it is desired to treat the tissue by RF hyperthermia. The treatment region TR prior to treatment is shown in FIG. 7.

Figure 8:
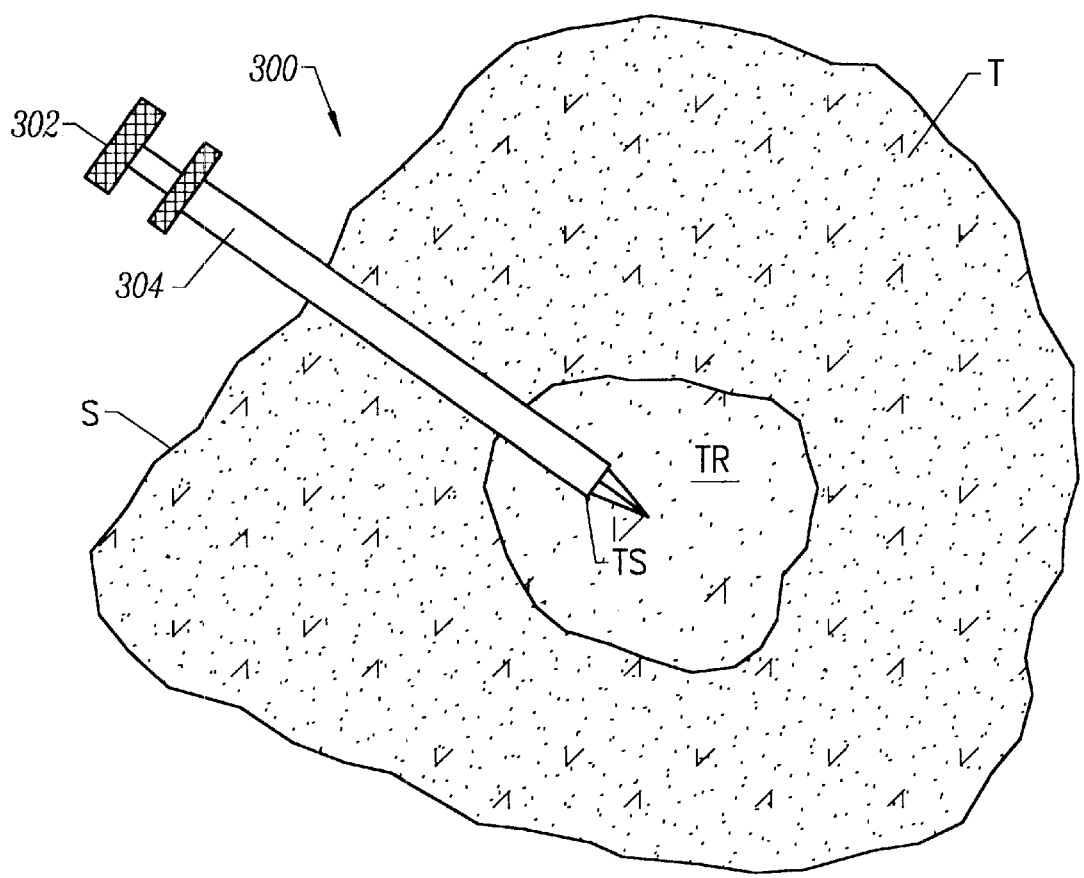
Figure 9:
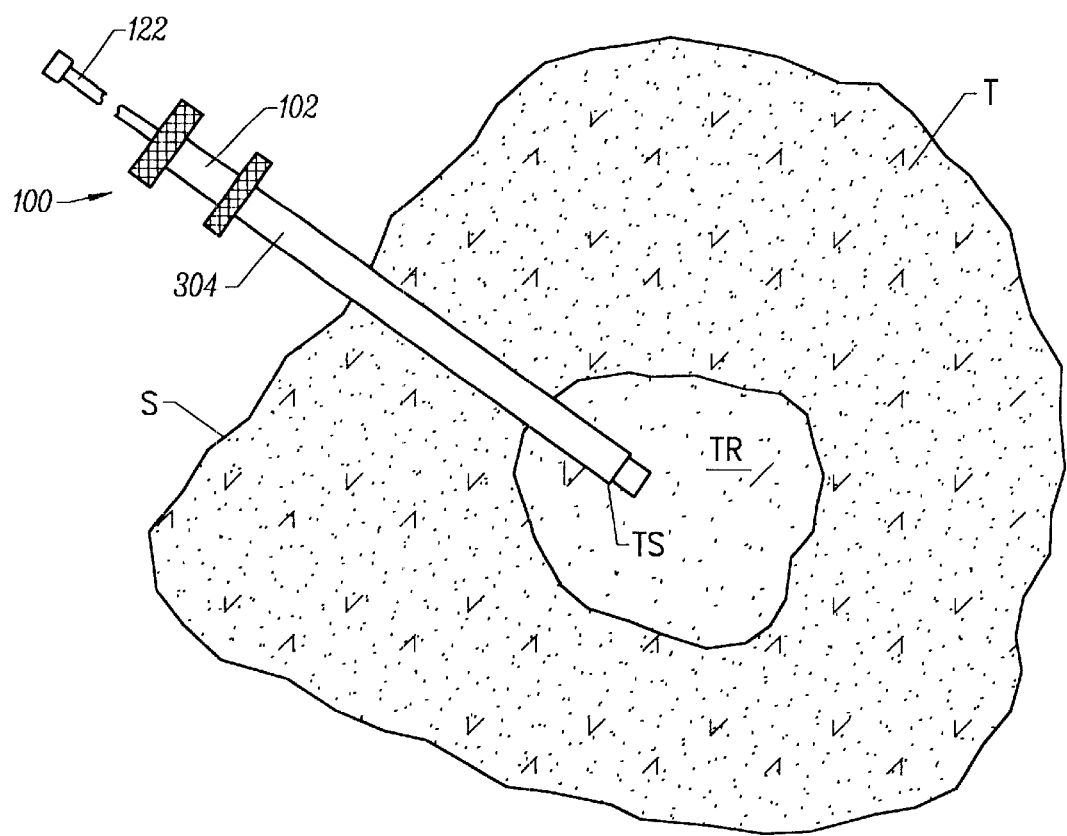

In order to introduce an electrode array according to the method of the present invention, a conventional sheath and obturator/stylet assembly 300 is introduced through the skin or organ surface S so that a distal end of the sheath lies at or within a target site TS within the treatment region, as shown in FIG. 8. In many cases, the sheath and obturator/stylet assembly 300 may be introduced percutaneously directly through the patient's skin. In other cases, however, it may be desirable to provide an open surgical incision or to place a trocar through the skin in order to introduce the stylet to the organ surface S. In either case, the obturator/stylet 302 is then removed from the sheath 304, leaving the sheath in place as shown in FIG. 9. The cannula 102 of probe system 100 may then be introduced through the lumen of sheath 304 so that a distal end advances from the sheath into the target region T, also as shown in FIG. 9.

An alternative placement method would utilize a cannula which incorporates a thin insulating film covering the exterior. Thus, the sheath/cannula may be directly inserted into target tissue without use of a separate sheath.

After the cannula 102 is properly placed, the shaft 122 will be distally advanced to deploy the electrodes 104 radially outwardly from the distal end of the cannula, as shown in FIG. 10. The shaft 122 will be advanced sufficiently so that the electrodes 104 fully evert in order to circumscribe substantially the entire treatment region TR. The core member 106 (FIG. 10) also advances distally into the tissue along a line which is axially aligned with the cannula 102.

A connector 140 at the proximal end of shaft 122 may then be connected to an electrosurgical power supply ES. Suitable power supplies are available from commercial suppliers as listed above. A second connecting cable 190 extends from the electrosurgical power supply ES to a dispersive plate electrode (not shown) on the patient for monopolar operation.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for heating a treatment region within solid tissue, said method comprising:
   introducing at least one electrode array to a target site within the treatment region;
   placing a counter electrode on or over a tissue surface remote from the treatment region;
   energizing the electrode array to initiate current flow between the electrode array and the counter electrode;
   increasing the power of electrode energization to a elevated power level at which an abrupt increase in electrode-tissue interface impedance is observed;
   reducing power sufficiently below said elevated level to permit the electrode-tissue interface impedance to decrease; and
   reenergizing the electrode at a level below said elevated level.

2. A method as in claim 1, wherein the electrode is energized with radio frequency current.

3. A method as in claim 2, wherein the radio frequency current is supplied with a controlled voltage power supply, wherein the increase in impedance is observed as a decrease in delivered power.

4. A method as in claim 1, wherein the reenergizing step is continued until at least a portion of the solid tissue in the treatment region is necrosed.

5. A method as in claim 1, wherein the solid tissue is liver tissue, kidney tissue, lung tissue, bowel tissue, stomach tissue, pancreas tissue, breast tissue, uterine tissue, prostate tissue, and muscle tissue.

6. A method as in claim 1, wherein the electrode power is increased to a level in the range from 50 W to 200 W.

7. A method as in claim 1, wherein the electrode is reenergized at a power level from 50% to 90% of the maximum power level.

8. A method as in claim 1, wherein the electrode energizing step comprises energizing with a power level selected to be less than the level which results in the abrupt increase in electrode/tissue interface impedance.

9. A method as in claim 8, wherein the elevated power level is predetermined and the power is increased abruptly, said method further comprising measuring the time elapsed from initiating the power increase to observing the electrode-tissue interface impedance increase, wherein the level of reenergization power varies inversely with the length of elapsed time.

10. A method as in claim 9, further comprising increasing the power level abruptly a second time to a elevated power level, measuring the elapsed time from initiating the second power increase to observing an electrode-tissue interface impedance increase, reducing power sufficiently below the elevated power level to permit the electrode-interface impedance to decrease, and reenergizing the electrode at a level which varies inversely with the second length of elapsed time.

11. A method as in claim 1, wherein the power is increased over time until the abrupt increase in electrode-tissue interface impedance is observed, further comprising:
   determining the elevated power level at which the electrode-tissue interface impedance increase is observed;
   wherein the reenergization power level is a predetermined fraction of the maximum power level.

12. A method as in claim 10, wherein the power is increased linearly at a rate in the range from 10 W/min. to 15 W/min.

13. A method as in claim 10, wherein the power is increased non-linearly at a rate which increases within the range from 5 W/min. to 25 W/min.

14. A method as in claim 11, wherein the predetermined fraction is from 60% to 90%.

15. A system comprising:
   an electrosurgical power supply; and
   instructions setting forth the method of claim 1.

16. A computer program embodied in a tangible medium, wherein the program sets forth a method according to claim 1.

17. A method for energizing an electrode disposed at a target site within solid tissue, said method comprising:
   delivering radio frequency power between the electrode and a counter electrode on or over a tissue surface remote from the target site under constant voltage;
   monitoring a power level being delivered;
   increasing the power until reaching an elevated power level at which the power level abruptly decreases due to an increase in impedance between the electrode and the tissue;

reducing the power level sufficiently to allow the impedance to decrease; and restoring the current to the electrode at a power level below the elevated power level.

18. An improved method as in claim 17, wherein the electrode current is increased to a power level in the range from 50 W to 200 W.

19. An improved method as in claim 17, wherein the power is restored to a power level from 50% to 90% of the elevated power level.

20. A method as in claim 17, wherein the delivering step comprises energizing with a power level selected to be less than the level which results in the abrupt increase in electrode/tissue interface impedance.

21. A method as in claim 17, wherein the elevated power level is predetermined and the power is increased abruptly, said method further comprising measuring the time elapsed from initiating the power increase to observing the abrupt power level decrease, wherein the level of restored current varies inversely with the length of elapsed time.

22. A method as in claim 21, further comprising increasing the power level abruptly a second time to a elevated power level, measuring the elapsed time from initiating the second power increase to observing an abrupt power level decrease, reducing power sufficiently below the elevated power level to permit the electrode-tissue impedance to decrease, and restoring current to the electrode at a level which varies inversely with the second length of elapsed time.

23. A method as in claim 17, wherein the current is increased over time until the abrupt decrease in power level is observed, further comprising:

determining the elevated power level at which the power level is observed;

wherein the restored current level is a predetermined fraction of the elevated power level.

24. A method as in claim 23, wherein the power is increased linearly at a rate in the range from 10 W/min. to 15 W/min.

25. A method as in claim 22, wherein the power is increased non-linearly at a rate which increases within the range from 5 W/min. to 25 W/min.

26. A method as in claim 20, wherein the predetermined fraction is from 60% to 90%.

27. A system comprising:

an electrosurgical power supply; and instructions setting forth the method of claim 17.

28. A computer program embodied in a tangible medium, wherein the program sets forth a method according to claim 17.

29. An improved method for energizing an electrode disposed at a target site in tissue, said method being of the type wherein the electrode and a counter electrode disposed on or over a tissue surface remote from the target site are powered by a radio frequency power supply, wherein the improvement comprises increasing voltage to increase power delivered to the electrode to a predetermined level, monitoring power delivered between the electrode and the counter electrode until an abrupt drop in the delivered power is observed, and thereafter delivering current between the electrode and the counter electrode at a level which results in a power level below that at which the abrupt drop in power delivered was observed.

30. A method as in claim 29, wherein the electrode current is increased to a power level in the range from 50 W to 200 W.

31. A method as in claim 29, wherein the electrode current is thereafter delivered at a power level from 50% to 90% of the maximum power level.

32. A method as in claim 29, wherein the current is increased to a level preselected to result in the abrupt drop in power, further comprising measuring the time elapsed from initiating the current increase to observing the power decrease, wherein the current delivered thereafter is delivered at a level which varies inversely with the length of elapsed time.

33. A method as in claim 29, wherein the current is increased linearly over time, further comprising determining the current at which the abrupt power decrease occurs, wherein the current is delivered thereafter at a fraction of the level at which the power decrease occurred.

34. A method as in claim 33, wherein the current is increased linearly at a rate in the range from 10 W/min. to 15 W/min.

35. A method as in claim 33, wherein the power is increased non-linearly at a rate which increases within the range from 5 W/min. to 25 W/min.

36. A method as in claim 33, wherein the fraction is from 50% to 90%.

37. A system comprising:

an electrosurgical power supply; and instructions setting forth the method of claim 29.

38. A computer program embodied in a tangible medium, wherein the program sets forth a method according to claim 29.

39. An electrosurgical power supply comprising:

a radio frequency power source having a controlled voltage output and a connection for a tissue electrode and a connection for a counter electrode; and a computer program embodied in a tangible medium and configured to control the radio frequency power source so that said power source increases power to a maximum level where an abrupt rise in impedance occurs, at which time the power source reduces power below said maximum level sufficiently to permit the impedance to decrease, after which the power source increases power to a treatment level below the maximum power level.

40. An electrosurgical power supply as in claim 39, further comprising a counter electrode selected from the group consisting of dispersive or return electrodes and additional tissue electrodes.

41. An electrosurgical power supply as in claim 39, wherein the adjusting means initiates a cycle where it abruptly raises the power to a predetermined maximum level, determines the time elapsed from initiating the power increase to observing the abrupt rise in impedance, and determines the treatment power level based at least in part on the length of elapsed time.

42. An electrosurgical power supply as in claim 41, wherein the adjusting means repeats the cycle.

43. An electrosurgical power supply as in claim 39, wherein the adjusting means initiates a cycle where the power is increased over time until the abrupt increase in electrode-tissue interface impedance is observed, the maximum power level at which the abrupt impedance increase occurs is observed, and the treatment power level is determined as a fraction of the maximum power level.

44. An electrosurgical power supply as in claim 43, wherein the adjusting means increases power linearly over a rate in the range from 10 W/min. to 15 W/min.

45. An electrosurgical power supply as in claim 43, wherein the adjusting means increases power non-linearly at a rate which increases within the range from 5 W/min. to 25 W/min.

46. An electrosurgical power supply as in claim 43, wherein the predetermined fraction is from 50% to 90%.

47. An electrosurgical power supply as in claim 46, wherein the power source operates at a frequency in the range from 300 kHz to 1.25 MHz and a power level in the range from 10 W to 200 W.

48. An electrosurgical power supply as in claim 46, wherein the adjusting means comprises a programmable digital controller.

49. An electrosurgical power supply as in claim 48, wherein the adjusting means comprises a control program embodied in a tangible medium.

50. An electrosurgical power supply as in claim 46, wherein the adjusting means is responsive solely to the delivered power.

* * * * *